(12) United States Patent
Tao et al.

(10) Patent No.: US 9,500,654 B2
(45) Date of Patent: Nov. 22, 2016

(54) METHODS FOR IDENTIFYING PROTEIN-PROTEIN INTERACTIONS

(71) Applicant: Purdue Research Foundation, West Lafayette, IN (US)

(72) Inventors: Weiguo Andy Tao, West Lafayette, IN (US); Changdeng Hu, West Lafayette, IN (US); Lingfel Zeng, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/297,824

(22) Filed: Jun. 6, 2014

(65) Prior Publication Data
US 2014/0364329 A1 Dec. 11, 2014

Related U.S. Application Data
(60) Provisional application No. 61/832,187, filed on Jun. 7, 2013.

(51) Int. Cl.
G01N 33/68 (2006.01)
C12Q 1/68 (2006.01)
G01N 33/573 (2006.01)
C12Q 1/48 (2006.01)
C12Q 1/66 (2006.01)

(52) U.S. Cl.
CPC ............ *G01N 33/573* (2013.01); *C12Q 1/485* (2013.01); *G01N 33/6845* (2013.01); *G01N 33/6848* (2013.01); *G01N 2333/912* (2013.01)

(58) Field of Classification Search
None
See application file for complete search history.

(56) References Cited

U.S. PATENT DOCUMENTS
7,335,897 B2 2/2008 Takats et al.

FOREIGN PATENT DOCUMENTS
WO 2009/102766 A1 8/2009

OTHER PUBLICATIONS

Morell et al., "Protein complementation assays: Approaches for the in vivo analysis of protein interactions" 583 FEBS Letters 1684-1691 (2009).*
Kodama et al., "An improved biomolcular fluorescence compelmentation assay with a high signal-to-noise ratio" 49(5) BioTechniques 793-805 (2010).*
Cuatrecasas et al., "Affinity Chromatography" 40 Annual Review of Biochemistry 259-278 (1971).*
Shevchenko et al., "In-gel digestion for mass spectrometric characterization of proteins and proteomes" 1(6) Nature Protocols 2856-2860 (2006).*
Gingras et al., Analysis of protein complexes using mass spectrometry 8 Nature Reviews | Molecular Cell Biology 645-654 (2007).*
Gundry et al. (Curr Protoc Mol Biol. 2009; Chapter 10).
ESI; Fenn et al., Science, 246:64-71, 1989.
Yamashita et al., J. Phys. Chem., 88:4451-4459, 1984.
Carroll et al., Anal. Chem. 47:2369-2373, 1975.
Laiko et al. Anal. Chem., 72:652-657, 2000.
Tanaka et al. Rapid Commun. Mass Spectrom., 2:151-153, 1988.
Takats et al., Science, 306:471-473, 2004.
Cody et al., Anal. Chem., 77:2297-2302, 2005.
Kogelschatz, Plasma Chemistry and Plasma Processing, 23:1-46, 2003.
Shiea et al., J. Rapid Communications in Mass Spectrometry, 19:3701-3704, 2005.
Garcia et al., Neoplasia 8, 523-533, doi:10.1593/neo.05745 (2006).
Unni, E. et al., Cancer Res 64, 7156-7168, doi:10.1158/0008-5472.CAN-04-1121 (2004).
Farini et al., Endocrinology 144, 1631-1643 (2003).
Canaff et al., Endocrinology 139, 1184-1196 (1998).
Kim et al., Journal of molecular endocrinology 34, 107-118, doi:10.1677/jme.1.01701 (2005).
Deng et al., American journal of cancer research 1, 834-844 (2011).
Deng et al., Cancer Res 68, 9663-9670, doi:10.1158/0008-5472.CAN-08-2229 (2008).
Cox et al., Cancer Res 59, 3821-3830 (1999).
Shyu et al., BioTechniques 40, 61-66 (2006).
Eng et al., J. Am. Soc. Mass Spectrom. 5, 976-989 (1994).
Elias et al., Nat Methods 2, 667-675 (2005).
Iliuk et al., Anal Bioanal Chem 393, 503-513, doi:10.1007/s00216-008-2386-0 (2009).
Tao et al., Curr Opin Biotechnol 14, 110-118 (2003).
Iliuk et al.,Mol Cell Proteomics 9, 2162-2172, doi:M110.000091 [pii] 10.1074/mcp.M110.000091 (2010).
Gao et al., J Biol Chem 276, 42219-42225, doi:10.1074/jbc.M105760200 (2001).
Liao et al., J Biol Chem 274, 37815-37820 (1999).
Shibatohge et al., J Biol Chem 273, 6218-6222 (1998).
Song et al., J Biol Chem 276, 2752-2757, doi:10.1074/jbc.M008324200 (2001).
Hu et al., Current Protocol in Cell Biology, 21.23.21-21.23.21 (2005).
Johannessen et al., Frontiers in bioscience : a journal and virtual library 12, 1814-1832, doi:2190 [pii] (2007).
Galan et al., J Am Soc Mass Spectrom 22, 319-328, 2011.
Trinkle-Mulcahy et al., J Cell Biol 183, 223-239, 2008.
Rothbauer et al., Nat Methods, 3:887-889, 2006.
Ong et al., Mol Cell Proteomics 1, 376-386, 2002.
Xue er al., Mol Cell Proteomics, 12(8):2354-69, 2013.
Surinova et al., Nat Protoc, (8):1602-19, 2013.
Picotti et al., Nat Methods, 9(6):555-66, 2012.
Lubonja R, et al. A public genome-scale lentiviral expression library of human ORFs. Yang X, Boehm JS, Yang X, Salehi-Ashtiani K, Hao T, Shen Y, Nature Methods. 2011.

(Continued)

*Primary Examiner* — Nancy J Leith
(74) *Attorney, Agent, or Firm* — Adam M. Schoen; Brown Rudnick LLP

(57) ABSTRACT

The invention generally relates to methods for identifying protein-protein interactions. In certain aspects, methods of the invention involve conducting a protein-fragment complementation assay on a sample to form a protein-protein complex between two proteins in the sample that only transiently interact under physiological conditions, separating the complexes from the sample, and analyzing a protein of the complex using a mass spectrometry technique.

19 Claims, 11 Drawing Sheets

(56) References Cited

OTHER PUBLICATIONS

Torti, D. & Trusolino, L. Oncogene addiction as a foundational rationale for targeted anti-cancer therapy: promises and perils. EMBO Mol Med 3, 623-636, doi:10.1002/emmm.201100176 (2011).
Kerppola, T. K. Bimolecular fluorescence complementation (BiFC) analysis as a probe of protein interactions in living cells. Annu Rev Biophys 37, 465-487, doi:10.1146/annurev.biophys.37.032807. 125842 (2008).
Hu, C. D., Chinenov, Y. & Kerppola, T. K. Visualization of interactions among bZIP and Rel family proteins in living cells using bimolecular fluorescence complementation. Mol Cell 9, 789-798 (2002).
Hu, C. D., Grinberg, A. & Kerppola, T. Visualization of protein interaction in living cells using bimolecular fluorescence complementation (BiFC) analysis. Current Protocol in Cell Biology, 21.23. 21-21.23.21 (2005).
Hu, C. D., Grinberg, A. V. & Kerppola, T. K. Visualization of protein interactions in living cells using bimolecular fluorescence complementation (BiFC) analysis. Current protocols in cell biology / editorial board, Juan S. Bonifacino . . . [et al.] Chapter 21, Unit 21 23, doi:10.1002/0471143030.cb2103s29 (2006).
Hu, C. D. & Kerppola, T. K. Simultaneous visualization of multiple protein interactions in living cells using multicolor fluorescence complementation analysis. Nat Biotechnol 21, 539-545, doi:10. 1038/nbt816 (2003).
Shyu, Y. J. et al. Visualization of protein interactions in living Caenorhabditis elegans using bimolecular fluorescence complementation analysis. Nat Protoc 3, 588-596, doi:10.1038/nprot.2008.16 (2008).
Xue, L. et al. Sensitive kinase assay linked with phosphoproteomics for identifying direct kinase substrates. Proc Natl Acad Sci U S A 109, 5615-5620 (2012).
Statsuk, A. V. & Shokat, K. M. Covalent cross-linking of kinases with their corresponding peptide substrates. Methods Mol Biol 795, 179-190, doi:10.1007/978-1-61779-337-0_12 (2012).
Shaywitz, A. J. & Greenberg, M. E. Creb: a stimulus-induced transcription factor activated by a diverse array of extracellular signals. Annual review of biochemistry 68, 821-861, doi:10.1146/annurev.biochem.68.1.821 (1999).
Cho, Y. S. et al. A genomic-scale view of the cAMP response element-enhancer decoy: a tumor target-based genetic tool. Proc Natl Acad Sci U S A 99, 15626-15631, doi:10.1073/pnas. 242617799 (2002).
Yuan, T. C. et al. Androgen deprivation induces human prostate epithelial neuroendocrine differentiation of androgen-sensitive LNCaP cells. Endocrine-related cancer 13, 151-167, doi:10.1677/erc.1.01043 (2006).
Napoli, N. et al. Low serum levels of 25-hydroxy vitamin D in adults affected by thalassemia major or intermedia. Bone 38, 888-892, doi:10.1016/j.bone.2005.11.018 (2006).
Tao, W. A. et al. Quantitative phosphoproteome analysis using a dendrimer conjugation chemistry and tandem mass spectrometry. Nat Methods 2, 591-598 (2005).
Galan, J. A. et al. Quantitative analysis of snake venoms using soluble polymer-based isotope labeling. Mol Cell Proteomics 7, 785-799 (2008).
Iliuk, A., Martinez, J. S., Hall, M. C. & Tao, W. A. Phosphorylation assay based on multifunctionalized soluble nanopolymer. Anal Chem 83, 2767-2774, doi:10.1021/ac2000708 (2011).
Tao, W. A. Soluble polymer-based isotopic labeling (SoPIL): a new strategy to discover protein biomarkers? Expert Rev Proteomics 4, 603-607 (2007).
Iliuk, A. & Tao, W. A. Quantitative phospho-proteomics based on soluble nanopolymers. Methods Mol Biol 527, 117-129, ix, doi:10. 1007/978-1-60327-834-8_10 (2009).
Hu, L., Iliuk, A., Galan, J., Hans, M. & Tao, W. A. Identification of drug targets in vitro and in living cells by soluble-nanopolymer-based proteomics. Angew Chem Int Ed Engl 50, 4133-4136, doi:10. 1002/anie.201006459 (2011).
Shyu, Y. J., Liu, H., Deng, X. & Hu, C. D. Identification of new fluorescent protein fragments for bimolecular fluorescence complementation analysis under physiological conditions. BioTechniques 40, 61-66 (2006).
Pear, W. Transient transfection methods for preparation of high-titer retroviral supernatants. Current protocols in molecular biology / edited by Frederick M. Ausubel . . . [et al.] Chapter 9, Unit9 11, doi:10.1002/0471142727.mb0911s36 (2001).
Yu, Haiyuan et al. "High Quality Binary Protein Interaction Map of the Yeast Interactome Network", Science, Oct. 3, 2008; 322(5898): 104-110.

* cited by examiner

METHODS FOR IDENTIFYING PROTEIN-PROTEIN INTERACTIONS

RELATED APPLICATION

The present application claims the benefit of and priority to U.S. provisional patent application Ser. No. 61/832,187, filed Jun. 7, 2013, the content of which is incorporated by reference herein in its entirety.

GOVERNMENT SUPPORT

This invention was made with government support under GM088317 awarded by National Institutes of Health. The government has certain rights in the invention.

FIELD OF THE INVENTION

The invention generally relates to methods for analyzing a protein and protein-substrate interactions.

BACKGROUND

In living cells, complex processes are typically accomplished by highly specific binding interactions among functional cell components, most commonly involving one or more proteins. Understanding which proteins bind to one another, and under what circumstances, poses difficult unsolved problems. An approach to learning which proteins bind to each other to form protein complexes is to isolate functional protein complexes, or portions thereof, in order to identify their components.

However, the dynamic nature of cellular machineries is frequently built on transient and/or weak protein associations. Those low affinity interactions preclude stringent methods for the isolation and identification of protein networks around a protein of interest. In fact, most in vivo protein-protein binding is transient and occurs only briefly to facilitate signaling or metabolic function. Capturing or freezing those momentary contacts to study which proteins are involved and how they interact is difficult.

For example, protein kinases and their substrates represent the largest signaling network that regulates multiple cellular functions. Deregulation of kinase activity has emerged as a major mechanism in numerous diseases. Kinase signaling cascades involve a complicated array of interconnected networks that are reprogrammed in response to disease events and in the presence of inhibitors. Typical, high throughput approaches such as yeast two-hybrid screening or mass spectrometry-based immunoaffinity purification are ineffective for the identification of unknown kinase substrates due to high false-positive rates and inability to detect their transient, dynamic interactions.

SUMMARY

The invention provides a high-throughput platform that combines a protein-fragment complementation assay with mass spectrometry to isolate and analyze proteins in a sample that only transiently interact under physiological conditions, such as upstream kinases and their substrates. The stability of a fused protein in the protein-fragment complementation assay allows transient and weak protein-protein (e.g., substrate-kinase or other enzyme-substrate) pairs to be isolated in the form of a very stable complex that can be easily isolated using moieties that only recognize the fused protein. Mass spectrometry allows for the unambiguous sequencing of interacting proteins and also provides the ability to distinguish specific interacting partners from false identifications through quantitative proteomics.

In certain aspects, the invention provides methods for analyzing a protein that involve conducting a protein-fragment complementation assay on a sample to form a protein-protein complex between two proteins in the sample that only transiently interact under physiological conditions. The complexes from the sample are separated, and a protein of the complex is analyzed using a mass spectrometry technique.

Any protein-fragment complementation assay known in the art may be used with methods of the invention. An exemplary protein-fragment complementation assay is a bimolecular fluorescence complementation assay. In these embodiments, methods of the invention may additionally involve observing the sample for presence of a fluorescent signal, thereby indicating formation of the protein-protein complex.

After formation of the protein-protein complexes, those complexes are separated from remaining components of the sample. Any separation technique known in the art may be used to accomplish the separating. An exemplary technique involves detecting a fluorescent signal in cells, thereby indicating formation of the protein-protein complex, and then using standard cell sorting techniques to isolate cells in which complexes have been detected. Another separation technique involves exposing the complexes to one or more solid supports, each solid support including a moiety that specifically binds a fused form of two protein fragments used in the protein-fragment complementation assay, and washing away remaining components of the sample. The moiety may be any moiety that specifically binds a fused form of two protein fragments used in the protein-fragment complementation assay. Exemplary moieties include antibodies and aptamers. In an exemplary embodiment, the moiety is an antibody that specifically binds the fused form of the two protein fragments. For example, in certain embodiments, the fused form of the protein fragments is a Yellow Fluorescence Protein (YFP), and the antibody is an anti-YFP antibody. In other embodiments, the fused form of the protein fragments is Venus, and the antibody is an anti-Venus antibody. In other embodiments, the fused form of the two protein fragments includes a first member of a binding pair, and the moiety is a second member of the binding pair. The solid support may be any solid support, such as beads, a planar substrate, a column, etc. In certain embodiments, the solid supports are beads. In certain embodiments, prior to the analyzing step, the method further includes eluting the complexes from the solid supports, and digesting the proteins to form peptides.

Once isolated, at least one of the proteins in the complex is analyzed using a mass spectrometry technique. Any mass spectrometry technique known in the art may be used for the analysis, and the technique used will depend on the properties of the target protein.

Another aspect of the invention provides methods for analyzing a protein that involve conducting a protein-fragment complementation assay on a sample to form a protein-protein complex between two proteins in the sample that only transiently interact under physiological conditions, in which the assay is conducted in the presence of a competitor. The complexes from the sample are separated, and a protein of the complex is analyzed using a mass spectrometry technique.

DETAILED DESCRIPTION

Figure 1:
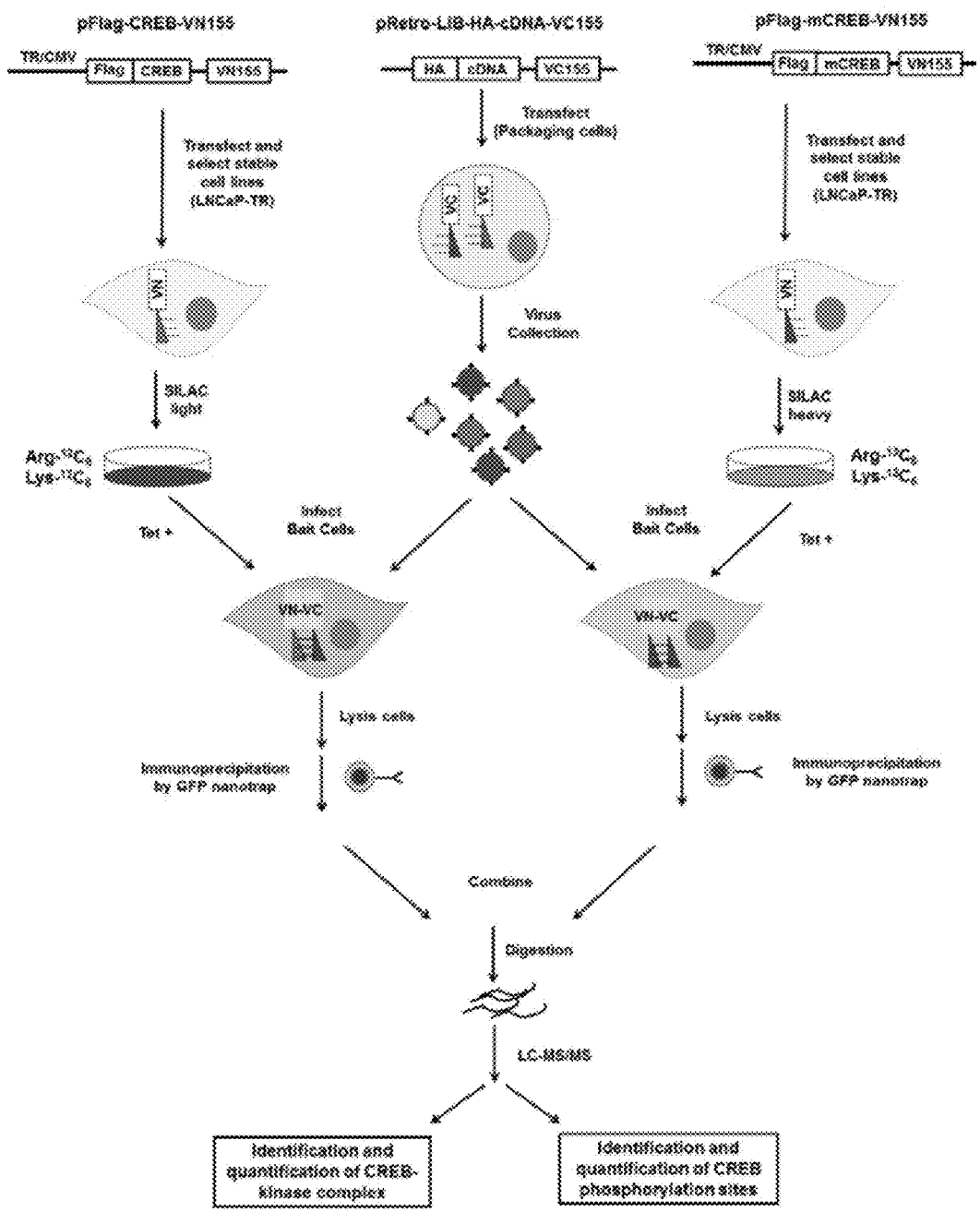
FIG. 1 is a schematic illustration of overall fluorescence complementation mass spectrometry (FCMS) strategy for identifying cAmp response element-binding protein (CREB) kinases.

The invention generally relates to methods for analyzing a protein. In certain aspects, the invention provides methods for analyzing a protein that involve conducting a protein-fragment complementation assay on a sample to form a protein-protein complex between two proteins in the sample that only transiently interact under physiological conditions. The complexes from the sample are separated, and a protein of the complex is analyzed using a mass spectrometry technique.

Methods of the invention address multiple issues with current approaches. For example, typical immunoprecipitation/mass spectrometry-based methods are ineffective to identify transient kinase-substrate pairs and also result in the co-isolation of high percentage of background proteins. Methods of the invention overcome such problems by using protein-fragment complementation assays. Products of a using protein-fragment complementation assay are essentially irreversible and therefore harsh washing condition (e.g., 5M NaCl and RIPA buffer) can be applied during the separating step to remove components of the sample that may lead to false positives. With minimized high abundant non-specific proteins that can compromise proteomic analysis, it is believed that methods of the invention will have a sensitivity that will reach sub-fetomole level.

Additionally, methods of the invention are able to address false positive identifications through use of quantitative measurement by mass spectrometry. For example, this is particularly true for the cAmp response element-binding protein (CREB) system in which multi-site phosphorylation of CREB by a diversity of protein kinases has been previously reported. Methods of the invention can not only identify distinctive CREB kinases under different physiological conditions, but also identify the sites of phosphorylation on CREB. This provides significant information to understand the diversity of signals to which CREB can respond on the molecular level. Methods of the invention can be used to identify upstream kinases of any substrate and applied to any transient protein-protein interaction.

Methods of the invention may be used to analyze any proteins that only transiently interact under physiological conditions, such as upstream kinases and their substrates. Normal physiological conditions in the human body refers to normal conditions within mammalian tissue or body fluid under which biological reactions occur in the absence of environmental stressors. Normal Physiological conditions are generally a pH of about 7 to about 8, preferably between 7.3 and 7.6, and a temperature of about 35° C. to about 38° C., preferably 37° C. The normal concentration of sodium in the blood plasma is 136-145 mM.

Any protein-fragment complementation assay known in the art may be used with methods of the invention. An exemplary protein-fragment complementation assay is a bimolecular fluorescence complementation assay. The bimolecular fluorescence complementation assay is based on the association of fluorescent protein fragments that are attached to components of the same macromolecular complex. Proteins that are postulated to interact are fused to unfolded complementary fragments of a fluorescent reporter protein and expressed in live cells. Interaction of those proteins bring the fluorescent fragments within proximity, allowing the reporter protein to reform in its native three-dimensional structure and emit its fluorescent signal. This fluorescent signal can be detected and located within the cell using an inverted fluorescence microscope that allows imaging of fluorescence in cells. In addition, the intensity of the fluorescence emitted is proportional to the strength of the interaction, with stronger levels of fluorescence indicating close or direct interactions and lower fluorescence levels suggesting interaction within a complex. Therefore, through the visualization and analysis of the intensity and distribution of fluorescence in these cells, one can identify both the location and interaction partners of proteins of interest.

After formation of the protein-protein complexes, those complexes are separated from remaining components of the sample. Any separation technique known in the art may be used to accomplish the separating. An exemplary technique involves detecting a fluorescent signal in cells, thereby indicating formation of the protein-protein complex, and then using standard cell sorting techniques to isolate cells in which complexes have been detected.

Another separation technique involves exposing the complexes to one or more solid supports, each solid support including a moiety that specifically binds a fused form of two protein fragments used in the protein-fragment complementation assay, and washing away remaining components of the sample. This approach overcomes certain problems with prior art assays. While typical protein-fragment complementation methods require lengthy procedures, including cell sorting, to identify unknown interacting partners. The use of the separation technique just described allows for the isolation of interacting proteins in high efficiency.

The moiety may be any moiety that specifically binds a fused form of two protein fragments used in the protein-fragment complementation assay. Exemplary moieties include antibodies and aptamers. In an exemplary embodiment, the moiety is an antibody that specifically binds the fused form of the two protein fragments. For example, in certain embodiments, the fused form of the protein fragments is a Yellow Fluorescence Protein (YFP), and the antibody is an anti-YFP antibody. In other embodiments, the fused form of the two protein fragments includes a first member of a binding pair, and the moiety is a second member of the binding pair. Exemplary binding pairs include biotin/streptavidin, dintrophenol/anti-dinitrophenol, digoxigenin/anti-digoxigenin, and other antigen/antibody or receptor binding pairs. The solid support may be any solid support, such as beads, a planar substrate, a column, etc.

Once isolated, at least one of the proteins in the complex is analyzed using a mass spectrometry (MS) technique. Typically, the protein complexes are eluted from the solid support and the protein is first broken up into peptides, either by chemical or enzymatic digestion, prior to MS analysis. The MS analysis is performed on the individual peptides, and the information is then stitched together to reveal the protein identity and/or characteristics (e.g., co-and post-translational modifications or isoforms). Important steps in this strategy include the preparation of the protein sample for digestion, enrichment for any particular peptides of interest, and cleanup or desalting of the final peptide mixture prior to MS analysis. Gundry et al. (Curr Protoc Mol Biol. 2009; Chapter 10), the content of which is incorporated by reference herein its entirety, provides methods for preparing proteins for MS analysis.

Any mass spectrometry technique known in the art may be used for the analysis, and the technique used will depend on the properties of the target protein. Exemplary mass spectrometry techniques that utilize ionization sources at atmospheric pressure for mass spectrometry include electrospray ionization (ESI; Fenn et al., Science, 246:64-71, 1989; and Yamashita et al., J. Phys. Chem., 88:4451-4459, 1984); atmospheric pressure ionization (APCI; Carroll et al., Anal. Chem. 47:2369-2373, 1975); and atmospheric pressure matrix assisted laser desorption ionization (AP-MALDI; Laiko et al. Anal. Chem., 72:652-657, 2000; and Tanaka et al. Rapid Commun. Mass Spectrom., 2:151-153, 1988). The content of each of these references in incorporated by reference herein its entirety.

Exemplary mass spectrometry techniques that utilize direct ambient ionization/sampling methods include desorption electrospray ionization (DESI; Takats et al., Science, 306:471-473, 2004 and U.S. Pat. No. 7,335,897); direct analysis in real time (DART; Cody et al., Anal. Chem., 77:2297-2302, 2005); Atmospheric Pressure Dielectric Barrier Discharge Ionization (DBDI; Kogelschatz, Plasma Chemistry and Plasma Processing, 23:1-46, 2003, and PCT international publication number WO 2009/102766), and electrospray-assisted laser desoption/ionization (ELDI; Shiea et al., J. Rapid Communications in Mass Spectrometry, 19:3701-3704, 2005). The content of each of these references in incorporated by reference herein its entirety.

Methods of the invention are now exemplified for the isolation of upstream kinases. Such exemplification does not limit the methods to isolation of upstream kinases and one of skill in the art will recognize that the exemplified method below can be applied to any proteins that transiently interact with each other by making minor changes to the assay that would be routine to one of skill in the art. In this embodiment, CREB provides a unique and important model system. CREB binds the consensus cAMP response element (CRE) to regulate gene transcription and has been implicated in prostate cancer growth (Garcia et al., Neoplasia 8, 523-533, doi:10.1593/neo.05745 (2006)), acquisition of androgen independent growth (Unni, E. et al., Cancer Res 64, 7156-7168, doi:10.1158/0008-5472.CAN-04-1121 (2004)), cAMP-induced neuroendocrine cell differentiation (NED) (Farini et al., Endocrinology 144, 1631-1643 (2003); and Canaff et al., Endocrinology 139, 1184-1196 (1998)), and transcription of prostate-specific antigen (Kim et al., Journal of molecular endocrinology 34, 107-118, doi:10.1677/jme.1.01701 (2005)). Previous work has shown that CREB is constitutively phosphorylated at Ser133 and other sites in the cytoplasm and ionizing radiation (IR) increases CREB phosphorylation in the nucleus (Deng et al., American journal of cancer research 1, 834-844 (2011); and Deng et al., Cancer Res 68, 9663-9670, doi:10.1158/0008-5472.CAN-08-2229 (2008)). Given that CREB phosphorylation at Ser133 is essential for its transcriptional activity and CREB can be phosphorylated on multiple sites by more than 15 different protein kinases (Cox et al., Cancer Res 59, 3821-3830 (1999)), identifying the physiological protein kinases that can associate with and phosphorylate CREB in response to IR will gain insight into the molecular mechanisms by which IR induces NED in prostate cancer cells. More importantly, the identified protein kinases could serve as molecular targets for development of therapeutic approaches targeting IR-induced NED. To further provide evidence that FCMS is generally applicable, a constructed library will be used to identify the upstream protein kinases of signal transduce and activator of transcription 3 (STAT3). STAT3 is activated at high frequency in clinical tumor samples through many cytokines and growth factors at the single tyrosine residue Tyr705 by protein kinases Janus kinase (JAK) or Src. On the other hand, STAT3 can also be phosphorylated at Ser727 by multiple serine protein kinases such as MAPK, mTOR, PKC, and CDK5 (29). Phosphorylation at Ser727 can further enhance the transcriptional activity of STAT3. Current approaches to target deregulated STAT3 activation effectively, however, remain an important scientific and clinical challenge. Identification of active STAT3 kinases specific in tumors could serve as molecular targets for development of therapeutic approaches.

In this embodiment, the methods of the invention combine (BiFC and MS) to create a powerful platform to identify upstream kinases in high throughput, which is called fluorescence complementation mass spectrometry (FCMS). Important aspects of the invention include being the first high throughput method to identify unknown upstream kinases in normal cellular environment, FCMS may be used with YFP nanotrap to specifically isolate BiFC complexes to avoid cell sorting and other long experimental procedures, and the use of fluorescence complementation for affinity purification and mass spectrometric identification of kinase-substrate pairs allows for the visualize of the interaction, identify resulting phosphorylation events, and quantify the binding stoichiometry, leading to great sensitivity and low false discovery identifications.

In this embodiment, methods of the invention use CREB as the model system to exemplify the technology to identify direct upstream kinases in living cells, as illustrated in FIG. 1. Briefly, CREB and its kinases are fused to complementary fragments of fluorescence protein (such as YFP) and expressed in LNCaP prostate cancer cells. Interaction of CREB and its kinase will bring the non-fluorescent fragments within proximity, allowing the reconstituted fluorescent protein to emit its fluorescent signal. CREB-kinase complex are isolated for MS analysis for identification and quantification of kinases and phosphorylation sites on CREB.

Figure 2:
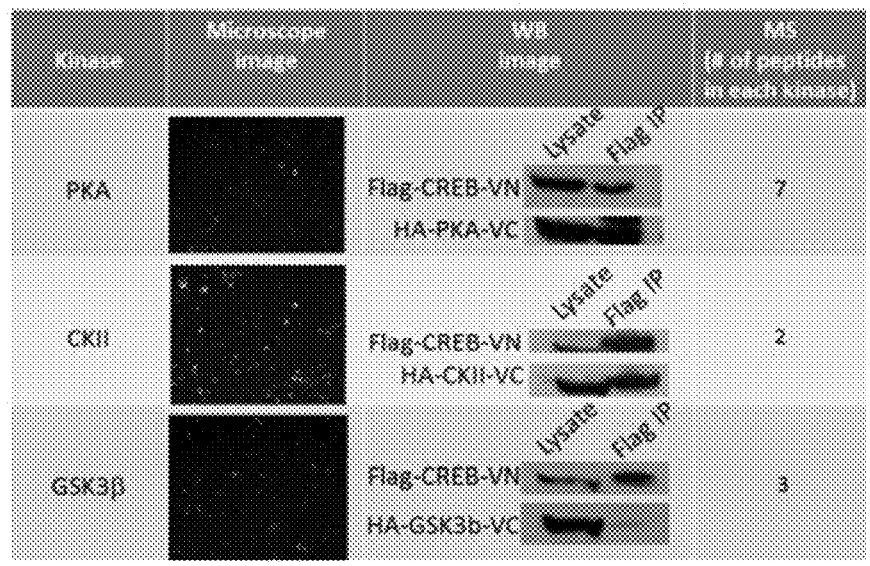
FIG. 2 is a set of gels showing identification of three CREB kinases through fluorescence imaging, WB and MS analysis.

BiFC-like constructions were made with additional epitope tags for affinity purification. Previous BiFC studies indicate that Venus-based analysis can be performed under physiological conditions and shows higher specificity compared to YFP-based assay (Shyu et al., BioTechniques 40, 61-66(2006)). CREB was fused with the fragment VN173 and the FLAG peptide epitope tag for affinity capture. Three known CREB kinases (PKA, GSK-3β, and CK-II) were fused to VC155, along with HA epitope tag for reverse affinity capture. Cells after infection for 48 h were examined by fluorescent microscopy. The Venus-based BiFC complexes have an excitation peak at 515 nm and an emission peak at 528 nm, and can be detected with a typical dissecting fluorescence microscope or inverted fluorescence microscopes. After observing positive protein-protein interactions by fluorescence microscopy, the cells were harvested and whole cell proteins were extracted. The CREB-kinase complex were isolated by incubating cell lysates with anti-FLAG antibodies immobilized on agarose beads. A harsh washing condition, such as 5M NaCl and RIPA buffer, can be applied to remove background proteins while preserving the complexes due to strong interactions between VN173 and VC155 fragments. Flag peptides or other denaturing agents (e.g. acid, base or detergents) were used to elute proteins off the beads. Proteins were digested with trypsin and peptides were analyzed by high resolution hybrid linear ion trap-ORBITRAP (LTQ-ORBITRAP Velos; ion trap mass analyzer consisting of an outer barrel-like electrode and a coaxial inner spindle-like electrode that traps ions in an orbital motion around the spindle) coupled to Eksigent nanoflow HPLC system. The MS data was subjected to database research against the human protein database for protein identification using SEQUEST/MASCOT software (Eng et al., J. Am. Soc. Mass Spectrom. 5, 976-989(1994); Elias et al., Nat Methods 2, 667-675(2005). The data show that all three kinases were positively identified by fluorescence imaging, Western Blotting, and MS analyses (FIG. 2).

A major advantages of the MS-based FCMS method is its unique capabilities of identifying potential post-translational modifications on interacting proteins and measuring interacting proteins quantitatively using stable isotope labeling or label-free methods (Iliuk et al., Anal Bioanal Chem 393, 503-513, doi:10.1007/s00216-008-2386-0 (2009); and Tao et al., Curr Opin Biotechnol 14, 110-118 (2003)). Two quantitative proteomic experiments will be devised to achieve high specificity of the FCMS technique. In a first approach, three known CREB kinases (positive controls) and negative controls (e.g., GAPDH fused to VC-155) will be constructed as described above and expressed in LNCaP cells. The same amount of cell extracts will be subjected to anti-HA immunoprecipitation. Note that, since the HA tag will be fused to kinases, different kinases will be the baits and the desirable interacting partner will be CREB. CREB peptides will be measured by MS through a stable isotope-labeled method or a label free method. Without being limited by any particular theory or mechanism of action, it is believed that specific interactions between CREB and its kinases will lead to higher amount of CREB isolation when specific kinases are used as baits than when negative controls as baits. Specific kinase-CREB interactions will be differentiated by comparing relative amount of CREB peptides in MS spectra.

In another approach, quantitative measurements of phosphorylation sites on CREB in CREB-kinase complexes will be used. Since multi-site phosphorylation of CREB by a diversity of protein kinases has been reported, MS experiments will be carried out to add another dimension of specificity by identifying CREB phosphorylation sites by the interacting kinase. Because phosphorylation is a low stoichiometry event, an enrichment step may be necessary to isolate phosphopeptides before MS analysis. Therefore, as an option, after the isolation and digestion of CREB-kinase complexes, a highly efficient phosphopeptide enrichment may be employed to enrich CREB phosphopeptides followed by MS analysis (Iliuk et al., Mol Cell Proteomics 9, 2162-2172, doi:M110.000091 [pii] 10.1074/mcp.M110.000091 (2010)). Again, a stable isotope-labeled method or a label-free method will be employed to compare phosphorylation changes on CREB after transfection with known kinases or negative controls. Initially, cells were treated with Forskolin to activate PKA and MS analysis identified four CREB peptides, including three phosphorylation sites S114, S142 and S143.

Figure 3:
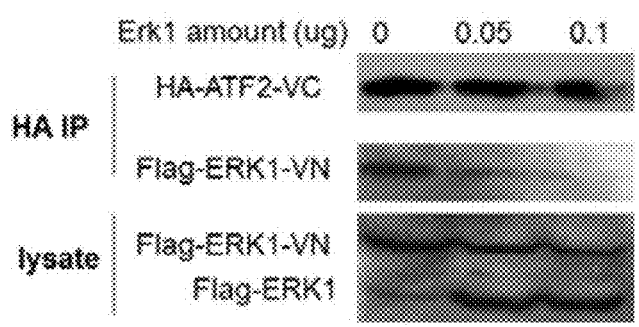
FIG. 3 is a set of gels showing results of a competition assay of Erk1-VN173 and ATF2-VC155 interaction using different amount untagged Erk1.

One important consideration for fluorescent-based protein-fragment complementation methods is the possibility of independent fluorescent protein fragment associations. Without proper controls the methods can have high false-positive protein interactions. Current controls include the use of mutants for the bait protein and varying the expression level of fusion proteins. However, these low throughput controls need to be adjusted based on each interacting pair. To improve the FCMS specificity, competitive binding will be introduced into the system to distinguish between true and false-positive protein interactions. As an example, in a separate study with kinase Erk1 and its kinase ATF2 (FIG. 3), increasing competition from untagged Erk1 expressed in the same cells, the signal of interacting Erk1-VN decreases in Western Blotting analysis in the anti-HA immunopurification experiment, suggesting specific interactions between Erk1 and ATF2. An improved strategy will be applied to thoroughly analyze CREB-kinase systems using both known kinases as positive controls and housekeeping proteins (such as GAPDH) as the potential negative control. In this case we will use inducible system to establish stable cell lines that can be induced to express untagged CREB. Then cells will be transfected normally with plasmids expressing FLAG-CREB-VN173 and HA-kinase-VC155. The expression of untagged CREB will be induced to compete against FLAG-CREB-VN173 for binding to HA-kinase-VC155.

One issue related to MS-based proteomics is the co-isolation of non-specific proteins that dominate low abundant proteins in the mass spectra, leading to low sensitivity and high false identifications. Methods of the invention can efficiently address that issue. Because BiFC complexes (VN-VC fusion in FIG. 1) are essentially irreversible, a far more harsh washing condition (e.g., 5M NaCl and RIPA buffer) can be applied than regular immunoprecipitation experiments, as long as it preserves the FLAG-antibody interactions.

Figure 4:
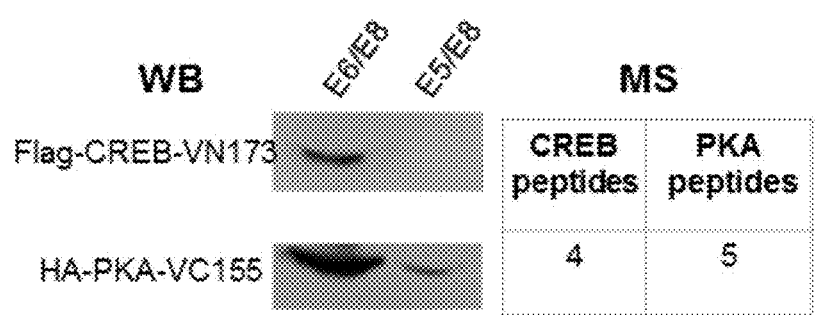
FIG. 4 is a set of gels showing WB and MS analysis of dilution experiments with CREB-PKA complex.

To determine the number of target cells for infection and the amount of virus to use for infection, preliminary dilution experiments were carried out to mimic a library screening method. Considering the total number of kinase cDNAs in the library, dilution experiments were carried out by diluting transfected cells expressing CREB-VN173 and PKA-VC155 with non-transfected cells at various ratios. As shown in FIG. 4, both Western Blotting and MS analyses were able to detect the bait protein (CREB) and its kinase PKA at the level when total $5 \times 10^5$ transfected cells (assuming 50% transfection rate) were present at the presence of ×500 higher background. This sensitivity is adequate for the proposed kinase library screening discussed below.

A human kinase open reading frame (ORF) collection will be utilized to construct a retrovirus-based kinase expression vectors. The collection was created by Broad Institute and distributed by Addgene. It consists of 559 distinct human kinases and kinase-related protein ORFs in pDONR-223 Gateway Entry vectors. All clones are clonal isolates and have been end-read sequenced to confirm identity. The cDNAs encoding all 559 kinases cannot be used directly by Gateway cloning, but with extensive experience in molecular cloning and retroviral expression system (Hu lab) (Gao et al., J Biol Chem 276, 42219-42225, doi:10.1074/jbc.M105760200 (2001); Liao et al., J Biol Chem 274, 37815-37820 (1999); Shibatohge et al., J Biol Chem 273, 6218-6222 (1998); and Song et al., J Biol Chem 276, 2752-2757, doi:10.1074/jbc.M008324200 (2001)), primers will be designed to amplify each of the cDNAs by removing the stop codon. Tet-ON inducible system will be first used to establish stable cell lines that can be induced to express FLAG-CREB-VN173 by tetracycline. The cDNA sublibrary encoding 559 kinases will be fused to VC155. Because fusion proteins can significantly reduce interaction-independent complementation (Hu et al., Current Protocol in Cell Biology, 21.23.21-21.23.21 (2005)), VC155 will be fused to the C-terminal end of kinase cDNAs. The cDNA encoding VC155 will be first subcloned into the pRetro-LIB, and then the cDNA encoding kinases was PCR amplified and subcloned upstream of the cDNA encoding VC155. This allows for expression of kinases as fusions with VC155. In the first step, stable cell lines that can be induced to express FLAG-CREB-VN173 will be cultured and induced with tetracycline first for 24 h, and then infected with retroviral kinase cDNAs. Cells after infection for 48 h will be examined by fluorescence microscopy. The expression level of fused proteins in transfected cells will be examined using Western Blotting on selected kinases.

Since the retrovirus titer of the kinase library will be critical to the screening, the experimental conditions will be optimized to generate high-titer retroviral particles (at least 106 units/ml).[40] The viral supernatant will be concentrated to at least $2.5 \times 10^9$ units/ml for transient transduction. At least $5 \times 10^8$ cells will be infected with $2.5 \times 10^9$ of viral particles (50 MOI). This will ensure that at least $1 \times 10^6$ cells will be infected with the virus encoding one kinase during the screening of the kinase library.

Conceivably, cells that have positive protein-protein interactions have to be sorted cleanly and genetic materials need to be isolated and sequenced to identify the potential interacting proteins. This can be a bottleneck and time consuming step to identify unknown protein-protein interactions in BiFC-like approaches. Proper controls are difficult to implement in high throughput screening method and it is difficult to evaluate the false positive rate. On the other hand, methods of the invention are particularly appealing because they not only provide a convenient strategy to identify interacting proteins without sorting and isolations, but also includes multiple elements to improve its specificity and estimate its false-positive rate. After a successful infection with the constructed kinase library, and the formation of BiFC complexes is verified by fluorescence microscopy, cells will be collected without sorting and isolation. Whole cell proteins will be extracted and subject to immunoaffinity purification and MS analysis, as described above and in FIG. 1. Multiple CREB kinases can be identified in a single experiment. False positive rate will be estimated through competitive binding from untagged CREB that can be inducibly expressed in cells, followed by quantitative proteomics to measure relative difference in interacting kinases. Kinases that show no difference with and without competition from untagged CREB will be considered as false discovery identification.

Previous studies indicate that multiple serine/threonine residues on of CREB can be phosphorylated by a diversity of protein kinases. The methods of the invention allow for identification of CREB-interacting kinases under different physiological conditions and identify the sites of phosphorylation on CREB. This provides significant information to understand the diversity of signals to which CREB can respond on the molecular level. For example, under ionizing radiation (IR) treatment, CREB in prostate cancer cells is hyper-phosphorylated on a time- and dose-dependent manner (Johannessen et al., Frontiers in bioscience: a journal and virtual library 12, 1814-1832, doi:2190 [pii] (2007)). It is likely that multiple kinases are involved in the phosphorylation, including ataxia-telangiectasia mutated (ATM). To screen for specifically IR-induced CREB kinase activity, we will use stable cell lines infected with the retroviral kinase cDNAs library for 24 h, and subject cells to IR (2Gy). Irradiated cells will be cultured for another 24 h and harvested to isolate CREB-kinase complexes for MS analysis. The success of FCMS analysis will be able to identify ATM and other active CREB kinases and identify potential phosphorylation sites on CREB. This will not only use CREB as a model system to establish the method, but also provide new information on CREB signaling in prostate cancer radiation.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Protein-protein interaction is a key mechanism in the regulation of signaling pathways in the cell. One of the most widely used high-throughput methods for obtaining protein-protein interaction data is affinity purification-mass spectrometry (AP-MS). However, in AP-MS, transient but biologically important interactions (e.g., kinase-substrate interactions) will probably be missed. Bimolecular fluorescence complementation (BiFC) assay is used widely for visualization of protein-protein interaction in living cells, which is based on complementation between fragments of certain fluorescent protein when they are brought together by an interaction between fused proteins. It is reported that the formation of the fluorescence complex is irreversible, which allows for the observation of the transient or weak interactions. The examples herein describe methods that combines protein-fragment complementation assays and MS to examine the kinase-substrate interactions by mass spectrometry.

Example 1

Plasmids Construction and Transfection

Kinases and substrates were cloned into pBiFC vectors (Typically pFlag-VN and pHA-VC). The plasmids were transfected to COS-7/293T cells using XtremeGene 9, and expressed for 24 hrs.

Example 2

Detection of BiFC Fluorescent Signal Using Microscopy

Cells were observed under an inverted fluorescence microscope equipped with objectives (20× and 60×), excitation source (mercury lamp), filter sets for Venus/eYFP (excitation at 500/20 nm; emission at 535/30 nm), filter sets for Cerulean/eCFP (excitation at 430/25 nm; emission at 470/30 nm).

Example 3

Separation of Complexes

Figure 5:
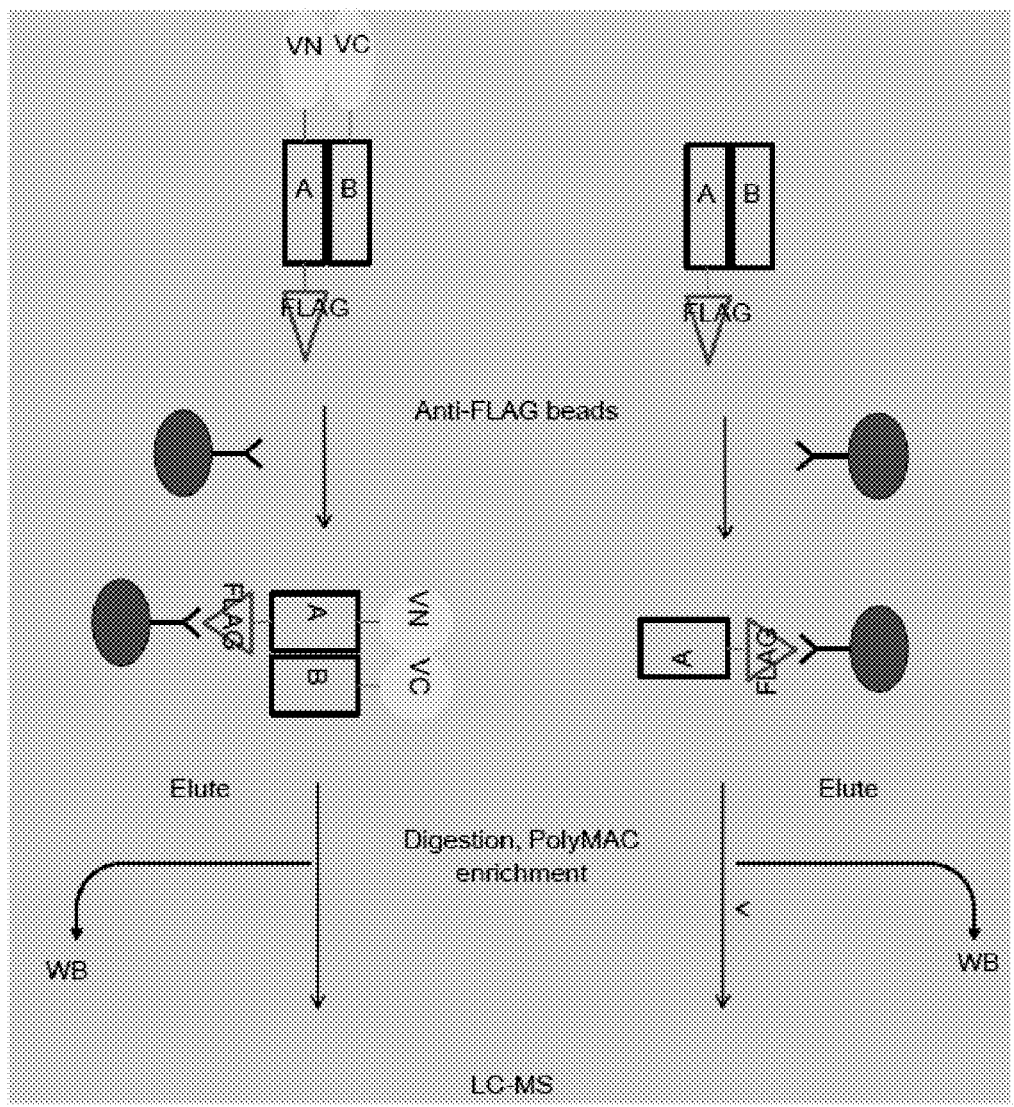
FIG. 5 is a schematic showing the work-flow of one example for protein-protein complex capture, purification, and analysis.

FIG. 5 is a schematic showing the work-flow for protein-protein complex capture, purification, and analysis. Cell were lysed and proteins were IP with Flag beads, HA beads or GFP nanotrap (specifically capture Venus protein). The beads were collected and washed.

Immobilized protein were reduced, akylated and digested. Polymer Based Metal Ion Affinity Chromatography (PolyMAC) was used for phosphopeptide enrichment. PolyMAC is further described in Tao et al. (U.S. patent application number 2010/0087008), the content of which is incorporated by reference herein in its entirety.

Peptides samples are dissolved in 8 ul of 0.1% formic acid. For samples that need to be quantified, internal standard peptide library were added. Experiments were performed on a Thermo LTQ-ORBITRAP-Velos instrument (ion trap mass analyzer consisting of an outer barrel-like electrode and a coaxial inner spindle-like electrode that traps ions in an orbital motion around the spindle). A 30-cm C-18 column was packed in-house and used. 30, 60 or 90 min gradient from 5%-40% buffer B was used to separate peptides. Buffer A: water with 0.1% FA; Buffer B: acetonitrile with 0.1% FA. The LC-MS/MS data were searched against IPI human database with search engine SEQUEST. Library Assisted eXtracted Ion Chromatogram (LAXIC) was used as quantitative MS method.

Example 4

Nanotrap

Figure 6:
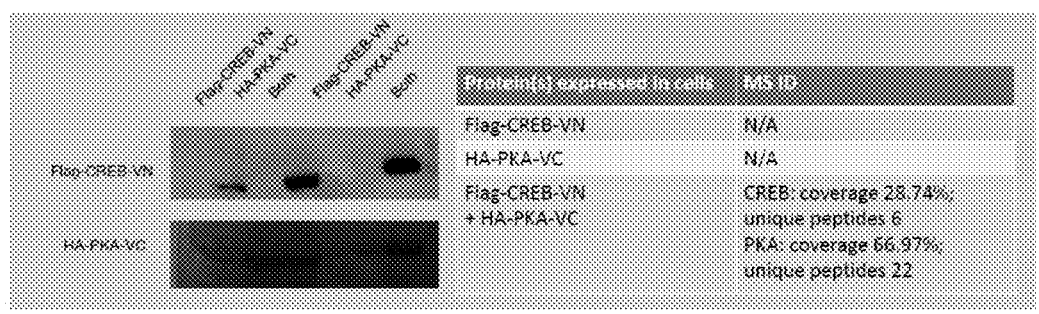
FIG. 6 shows GFP nanotrap IP, Western blot and MS data.

Flag-CREB/mCREB-VN and HA-kinases-VC were transfected to cells. By AP with GFP nanotrap, SILAC quantification, was used to discover bona fide upstream kinase of CREB. FIG. 6 shows that when CREB and PKA interact, VN and VC re-associate and can be specifically captured by a GFP nanotrap.

Example 5

Identifying Transient Interactions

Figure 7:
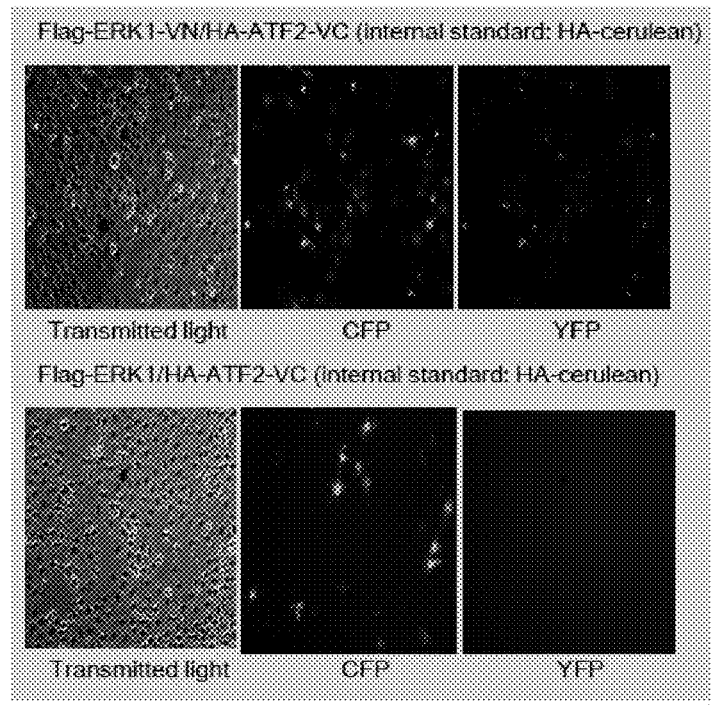
FIG. 7 shows results of a BiFC assay: ERK1 and ATF2 interaction.

Extracellular signal-regulated kinase 1 (ERK1) and its substrate transcription factor 2 (ATF2), Fos and Jun were chosen as the model system. FIG. 7 shows the fluorescence imaging when Flag-ERK1-VN/Flag-ERK1 and HA-ATF2-VC were co-transfected to cells. HA-Cerulean were transfected as internal standard to indicate the transfection efficiency. When ERK1 and ATF2 interact, VN and VC re-associate and emit yellow fluorescence.

Figure 8:
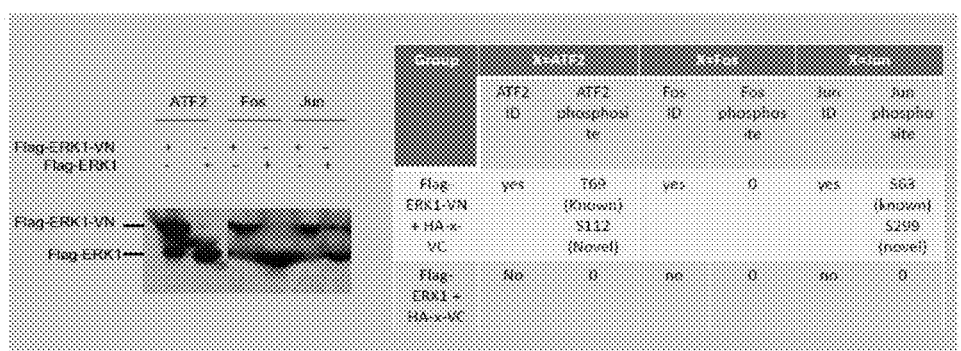
FIG. 8 shows Flag IP, Western blot and MS data.

Flag-ERK1-VN/Flag-ERK1 and HA-ATF2/Jun/Fos were co-transfected to cells. The experiment procedure as described above. After Flag IP, Western blot shows equal expression of Flag-ERK1-VN and Flag-ERK1 (FIG. 8). MS data shows fluorescent protein fragments are required for stabilize the interactions between ERK1 and its substrates, which enable MS to identify the preys and possible phosphosites (FIG. 8).

Figure 9:
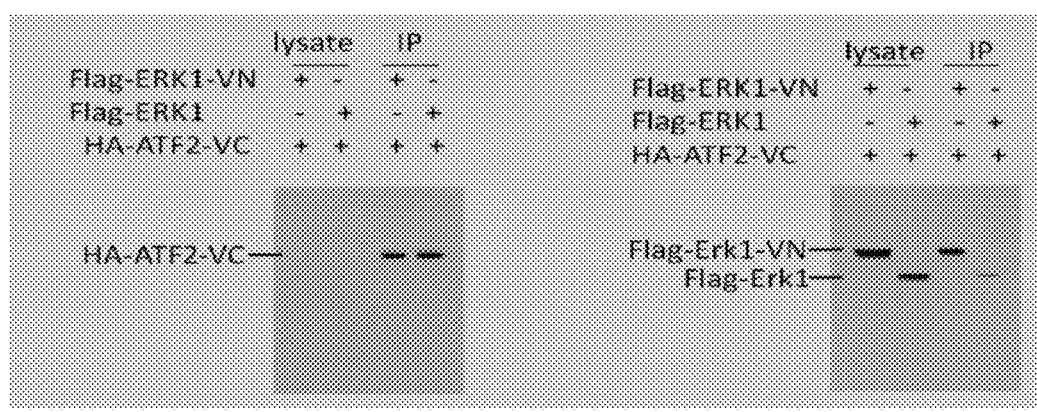
FIG. 9 shows HA IP, western blot result.

Western blot also showed stronger interaction between ERK1 and its substrates when they are fused with fluorescent protein fragments (FIG. 9).

Figure 10:
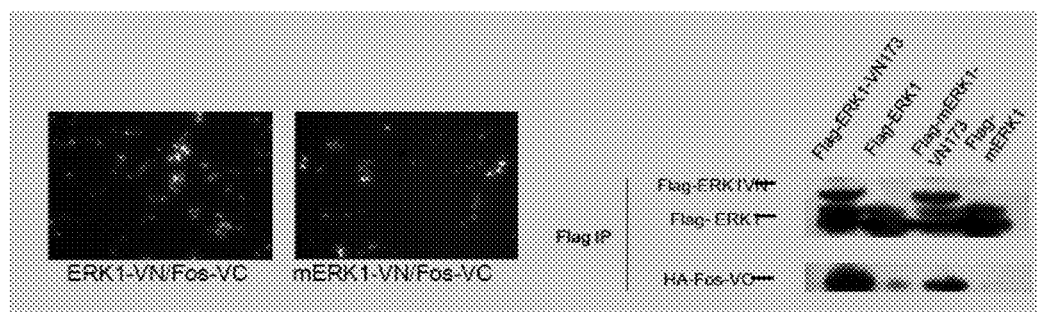
FIG. 10 shows fluorescence imaging and western blot: ERK1 vs. ERK1(L253A).

ERK1 (L253A) is the mutation in the FRS domain that disrupts its interaction with Fos. The data shows that Flag-ERK1(L253A)-VN has a weaker interaction with HA-Fos-VC than Flag-ERK1-VN (FIG. 10), indicating they are true interacting proteins. Quantitative MS indicated the ratio of Fos is wtERK1: mERK1 is 2:1, showing that methods of the invention can detect specific interactions.

Example 6

FCMS to Capture Upstream Kinases

Figure 11:
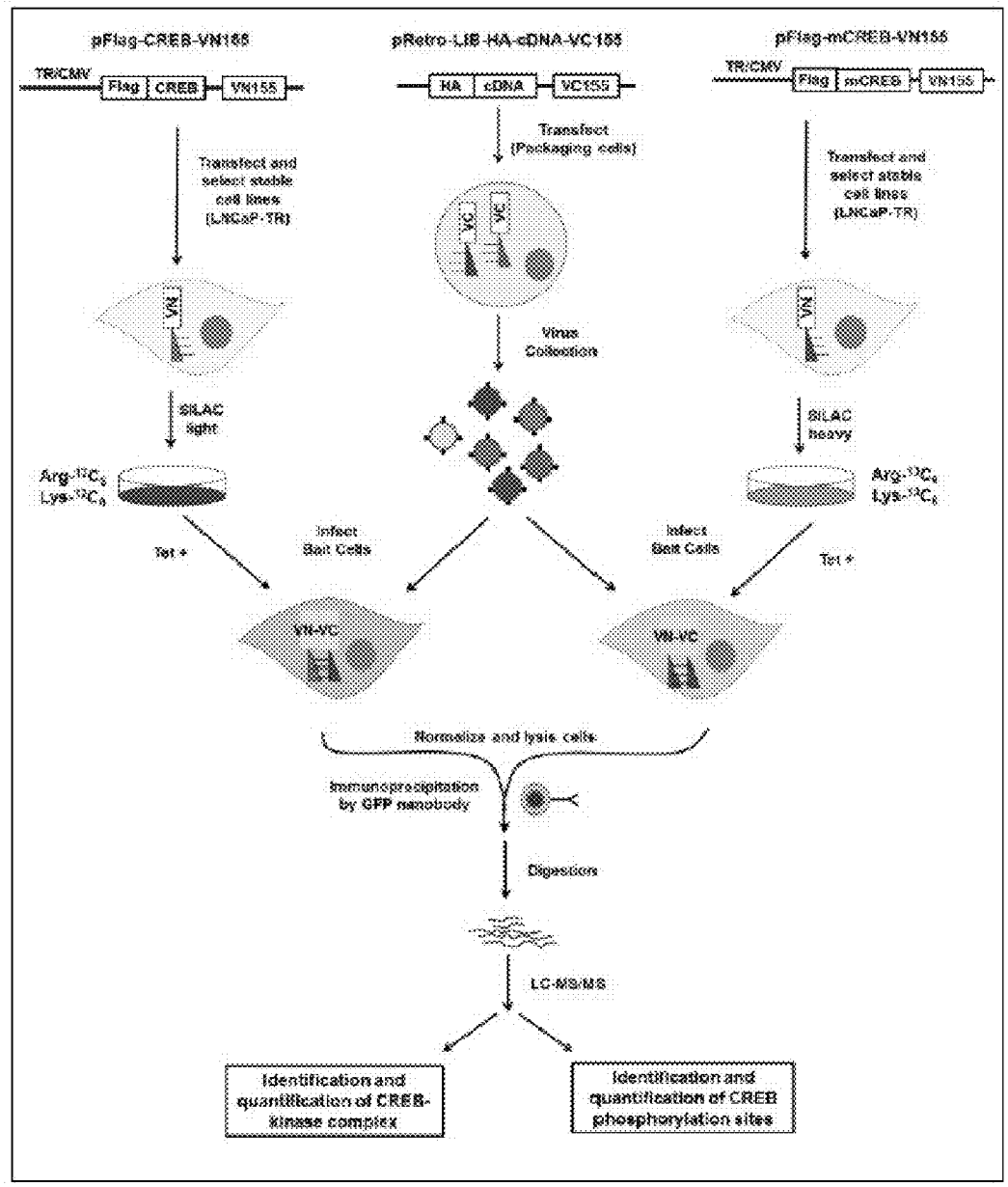
FIG. 11 is a schematic illustration of an overall FCMS strategy for identifying CREB kinases.

FIG. 11 illustrates an overview of methods of the invention for identifying direct upstream kinaases in a CREB model. Kinases such as CREB (or its mutant or deletion, mCREB) and a kinase library are fused to complementary fragments of fluorescent protein Venus, VN155 and VC155, respectively. LNCaP prostate cancer cells are transfected with CREB-VN155 or mCREB-VN-155, and stable cells are selected and then cultured in stable isotope-labeled media using "light" and "heavy" SILAC (Stable Isotope Labeling via Amino acids in Cell culture) (42, 43), respectively. The "light" SILAC sample is labeled with Lys-12C6 and Arg-12C6, while the "heavy" SILAC sample is labeled with Lys-13C6 and Arg-13C6. The differentially labeled LNCaP cells are further transfected with virus collections containing the kinase library-VC155 construction. Interaction of CREB and its kinase brings the non-fluorescent fragments within proximity, allowing the reconstituted fluorescent protein to emit its fluorescent signal. Cells are normalized and then combined. CREB-kinase complexes are isolated using anti-GFP nanobody immobilized on agarose beads which only recognizes and isolates VN155-VC155 containing proteins, but not the individual fragments. BiFC complexes are eluted from the beads, digested and peptides are analyzed by MS analysis. MS allows us to not only identify interacting kinases and phosphorylation sites on CREB, but also quantify relatively intensity of interacting proteins which will be used to differentiate specific interactions from nonspecific signals.

A. GFP Nanobody Specifically Isolated BiFC Complexes

Figure 12:
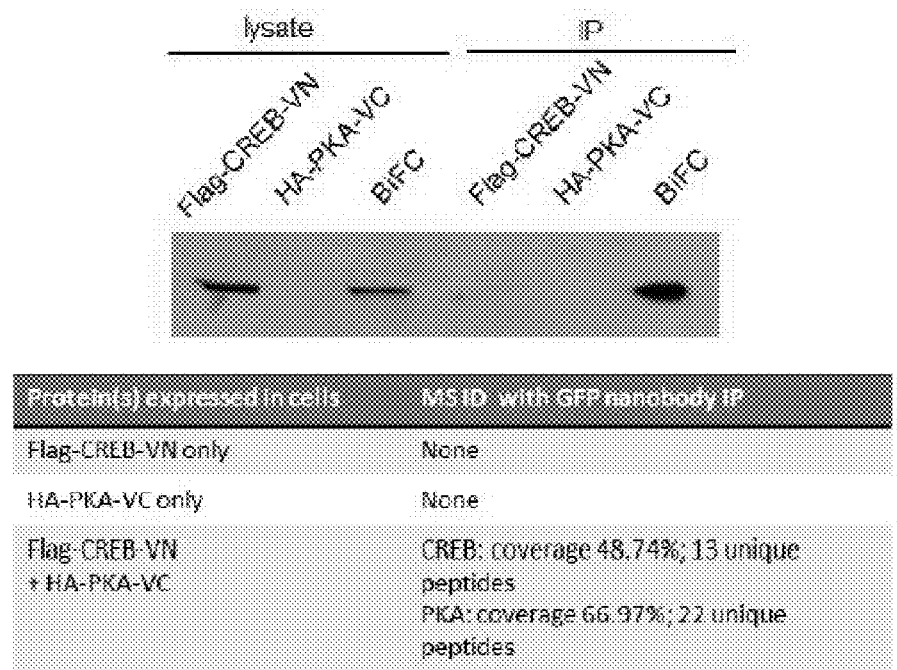
FIG. 12 shows specific isolation of CREB-PKA BiFC complex by anti-GFP nanobody through Western Blotting (top) and MS (bottom) experiment. The membrane was blotted using anti-Flag antibody.

In a classical BiFC experiment, the formation of BiFC complex is examined with fluorescent microscopy and accordingly, cells with the formation of BiFC complexes are sorted cleanly using FACS to screen unknown interacting proteins. The procedure is long, laborious, and not compatible with MS-based experiments due to limited quantity of materials available isolated via FACS. To solve that problem, methods of the invention may use a capture moiety that specifically recognizes BiFC complexes, but not individual fragments of the BiFC assay. An engineered single-chain anti-GFP antibody (GFP nanobody) was identified that specifically recognizes BiFC complexes but not individual fragments (Galan et al., J Am Soc Mass Spectrom 22, 319-328, 2011; Trinkle-Mulcahy et al., J Cell Biol 183, 223-239, 2008; and Rothbauer et al., Nat Methods, 3:887-889, 2006). GFP nanobody (or nanotrap) was originally developed to isolate proteins with GFP or YFP epitope tags in remarkably high efficiency (Rothbauer et al., Nat Methods, 3:887-889, 2006). As shown in FIG. 12, the Western Blotting results revealed GFP nanobody only isolates CREB-PKA BiFC complex specifically, not individual CREB-VN or PKA-VC proteins only. Consistent to the WB results, immunoaffinity purification using the GFP nanobody followed by MS analysis resulted in high coverage of CREB and PKA proteins from the CREB-PKA BiFC complex, but not in the CREB-VN or PKA-VC only cells. We also tested the GFP nanobody on other BiFC complexes and observed similarly high specificity. This data validates a method for isolating BiFC complexes without resorting to cell sorting which could require significant amount of time to obtain enough material for MS analysis.

B. Detection of Three Known CREB Kinases

Figure 13:
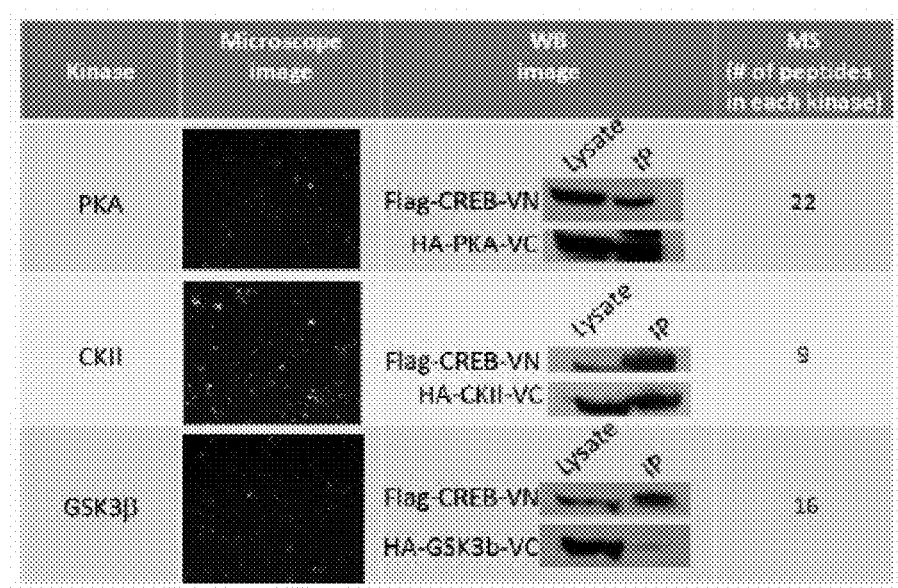
FIG. 13 shows identification of three CREB kinases through fluorescence imaging, Western Blotting and MS analysis.

Investigations were carried out to test the feasibility of FCMS using known CREB kinases (FIG. 13). Three known CREB kinases (PKA, GSK-3β and CK-II) were fused to VC155 along with HA epitope tag. CREB was fused with the fragment VN155 and the FLAG peptide epitope tag. Cells after infection for 48 h were examined by fluorescent microscopy. Cells were harvested, whole cell proteins were extracted and the CREB-kinase complexes were isolated by incubating cell lysates with GFP nanobody immobilized on agarose beads. Proteins were eluted off the beads, digested with trypsin, and peptides were analyzed by MS. The data show that all three kinases were positively identified by fluorescence imaging, Western Blotting, isolated by GFP nanobody and sequenced by MS analyses.

Figure 14:
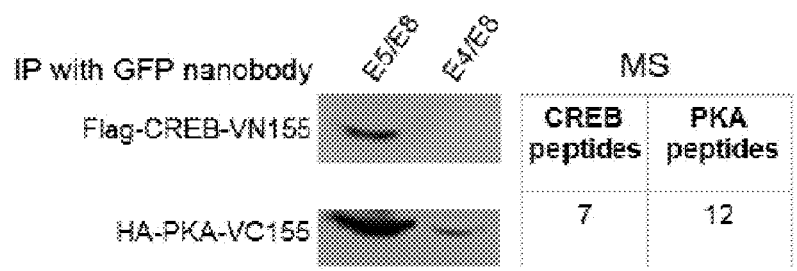
FIG. 14 shows Western Blot and MS analysis of dilution experiments with CREB-PKA BiFC complex.

C. Sensitivity Analysis to Differentiate Specific Interactions from Background Signals An important concern for high throughput screening is whether a method has sufficient sensitivity. To evaluate the feasibility and determine the number of target cells for infection and the amount of virus to use for infection, preliminary dilution experiments were carried out to mimic the library screening method. Considering the total number of kinase cDNAs in the library, dilution experiments were carried out by diluting transfected cells expressing CREB-VN155 and PKA-VC155 with non-transfected cells at various ratios. As shown in FIG. 14, both Western Blotting and MS analyses were able to detect the bait protein (CREB) and its kinase PKA at the level when total $5 \times 10^4$ transfected cells (assuming 50% transfection rate) were present at the presence of $\times 10^3$ higher background. This sensitivity is adequate for the proposed kinase library screening discussed in greater detail below.

Figure 15:
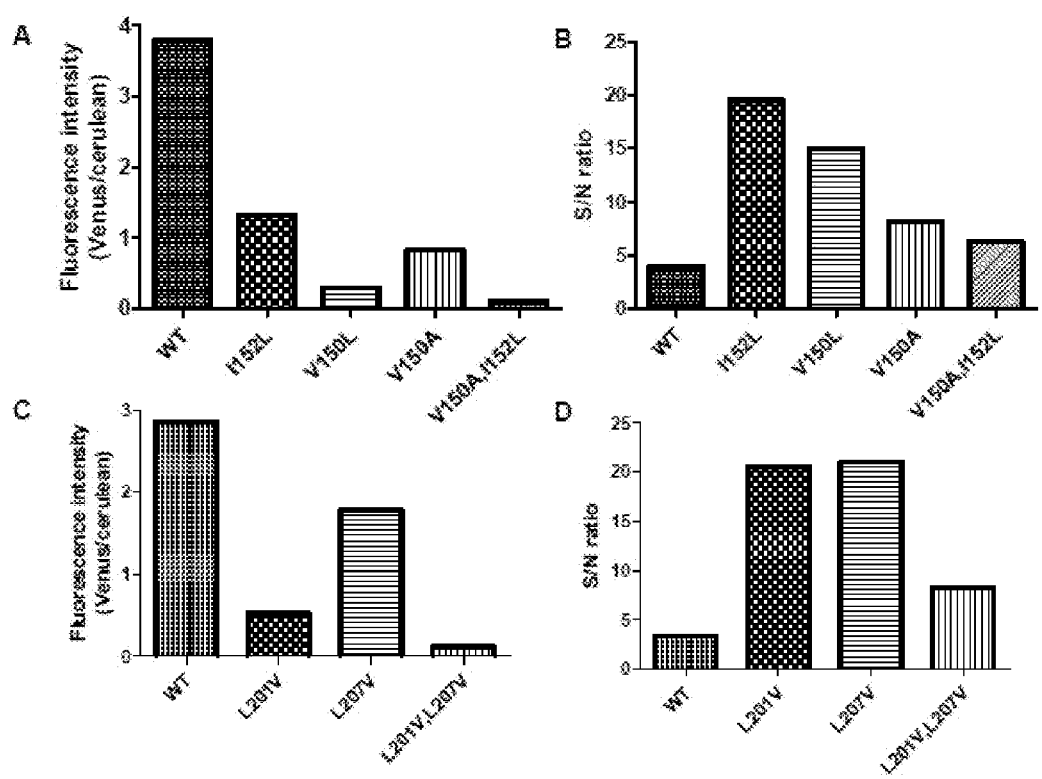
FIG. 15 panels A-D show the effect of mutations on self-assembly and signal-to-noise (S/N) ratio in Venus-based BiFC system. Indicated mutations were introduced into VN155 and paired with VC155 for analysis of (panel A) self-assembly (panel B) S/N analysis using bJun/bFos and the bJun/bFosΔZIP as a positive and negative interaction in COS-1 cells. Panels C and D. Similar experiments were performed to evaluate the effect of indicated mutations on self-assembly and S/N ratio when they were introduced into VC155.

D. Demonstration of VC155(L201V) as the Best Mutant Fragment for BiFC Analysis with Higher Signal-to-noise Ratio and Lower Self-assembly The Venus-based BiFC system has been widely used due to its higher fluorescence complementation efficiency and less sensitivity to environment. However, like all other fluorescent protein-based BiFC systems, the self-assembly between the two non-fluorescent fragments (VN155 and VC155) contributes to higher background signal. It has been found that the introduction of the I152L mutation into the VN155 fragment results in a significant reduction in self-assembly and an increase in signal to noise ratio (Kodama et al., Biotechniques, 49(5):793-805, 2010). The bJun/bFos interaction was used as a model system to complete a comparative analysis. While all mutations achieved a signal-to-noise ratio of at least 10, they reduced self-assembly to various degrees (FIG. 15). This analysis has identified VC155(L201V) as the best mutant that shows the highest signal-to-noise ratio but displays a lower self-assembly tendency. Thus, this mutant VC155 will be used for kinase cDNA library construction and for FCMS.

E. Results

In summary, the following evidence illustrates the ability to use methods of the invention to identify upstream kinases in a high throughput manner:

- Construct and characterization of BiFC expression vectors with CREB and three known kinases.
- The GFP nanobody is extremely specific and highly efficient for the isolation of BiFC complexes.
- Several known CREB-kinase BiFC complexes isolated by GFP nanobody can be detected by Western Blotting and MS analysis.
- The sensitivity of FCMS with known CREB kinases is adequate using 105 cells/kinase in the 103 higher background for transfection, indicating the feasibility of our proposed library screening containing 559 kinases.
- VN155 paring VC155(L201V) demonstrates higher signal-to-noise ratio with reduced background signal.

Example 7

Isolation of BiFC Complexes Using GFP Nanobody with CREB and Three Known CREB Kinases The GFP nanobody is an engineered variable single domain antibody fragment, VHH, and is small (2.4×4.5 nm; molecular mass 13 kDa; Rothbauer et al., Nat Methods, 3:887-889, 2006). It is highly specific for fluorescent proteins such as GFP and YFP and therefore provides a robust and highly efficient tool for the isolation of GFP or YFP fusion proteins (Galan et al., J Am Soc Mass Spectrom 22, 319-328, 2011; Trinkle-Mulcahy et al., J Cell Biol 183, 223-239, 2008; and Rothbauer et al., Nat Methods, 3:887-889, 2006). Anti-GFP antibodies (from several commercial sources) were initially used in an attempt to isolate BiFC complexes. However, they isolated not only BiFC complexes, but also VN- and VC-fused proteins in similar efficiency, and therefore are not appropriate for the purpose of harvesting BiFC complexes only.

The GFP nanobody was immobilized on agarose beads for the isolation of CREB-kinase complexes. The data in FIG. 12 show that the GFP nanobody specifically isolates BiFC complexes only, and no individual VN- or VC-fused protein. It was also found that the isolation of BiFC complexes using GFP nanobody is extremely fast. A typical immunoprecipitation experiment using classical antibodies usually requires multiple hours (sometimes overnight) for the capturing step. Using the GFP nanobody, it was found that it took less than five minutes to capture GFP/YFP or their fusion proteins. This feature is significant in this project because it can minimize false positive results from in vitro formation of BiFC complexes during the cell lysis and in vitro incubation period.

Previous studies indicated extremely strong affinity of GFP nanobody to GFP/YFP fusion proteins (Kd below 1 nM) (Galan et al., J Am Soc Mass Spectrom 22, 319-328, 2011; Trinkle-Mulcahy et al., J Cell Biol 183, 223-239, 2008; and Rothbauer et al., Nat Methods, 3:887-889, 2006). Similar strong affinity was observed between GFP nanobody and Venus BiFC complexes. This feature allows for the application of harsh washing conditions to remove background proteins while preserving the BiFC complexes (the interactions between VN155 and VC155 fragments are strong as well). For example, it was observed that BiFC complexes can withstand high salt concentration (5M NaCl) and a wide range of pH conditions (pH 4-10). Typical immunoprecipitation (IP)-based methods result in the co-isolation of high percentage of background proteins that are usually highly abundant and can overshadow low abundant proteins. It is expected that the high affinity of GFP nanobody can efficiently address the issue. This feature can also improve the sensitivity of the methods of the invention after removing high background proteins. Denaturing agents (e.g. strong acids like TFA; glycine with pH<4; detergents) can elute proteins off the beads.

As shown in FIG. 13, FLAG-CREB-VN155 were successfully constructed, along with three known CREB kinases (PKA, GSK-3β and CK-II) fused to VC155 and HA epitope tag. FLAG and HA tags are included for the purpose of detection. Cells after infection for 48 h will be examined by fluorescent microscopy. The Venus-based BiFC complexes have an excitation peak at 515 nm and an emission peak at 528 nm, and can be detected with a typical dissecting fluorescence microscope or inverted fluorescence microscopes. Once observing positive protein-protein interactions by fluorescence microscopy, we will harvest cells, whole cell proteins will be extracted and BiFC complexes will be isolated using GFP nanobody. The complexes will be eluted, digested with trypsin, and resulting peptides will be analyzed by high resolution hybrid linear ion trap-ORBITRAP (LTQ-ORBITRAP-Velos; ion trap mass analyzer consisting of an outer barrel-like electrode and a coaxial inner spindle-like electrode that traps ions in an orbital motion around the spindle) coupled to Eksigent nanoflow HPLC system. The MS data will be subjected to database research against the human protein database for protein identification using SEQUEST/MASCOT software (Eng et al., J. Am. Soc. Mass Spectrom. 5, 976-989 (1994); Elias et al., Nat Methods 2, 667-675 (2005)). Data will be filtered using appropriate false discovery rate (FDR), typically 1% in our studies. Due to the high isolation efficiency by GFP nanobody, the data show that the MS coverage of all three kinases was quite high (FIG. 13).

Example 8

Distinguishing Specific CREB-Kinase Interactions Through SILAC-Based Quantitative Proteomics The data herein have demonstrated that a new mutant in the VC fragment, VC155(L201V), can significantly improve signal-to-noise ratio and lower self-assembly. Therefore VC155(L201V) will be used in further investigations. In this Example, methods of the invention are used to identify phosphorylation sites on substrates and measure interacting proteins quantitatively, to distinguish specific CREB-kinase interactions. Quantitative proteomics can be achieved using stable isotope labeling or label-free methods (Ong et al., Mol Cell Proteomics 1, 376-386, 2002; and Xue er al., Mol Cell Proteomics, 12(8):2354-69, 2013). In this Example, a SILAC-based quantitative proteomic approach will be used to achieve high specificity of the FCMS technique (FIG. 11). In addition to the CREB-VN155 construction, CREB mutants or deletions fused with VN155 (mCREB-VN155) will also be construtced in parallel. The CREB mutants or deletions will be prepared within predicted CREB binding region, and a series of mutants and deletions to disrupt CREB-kinase interactions will be screened. Cells expressing CREB-VN155 and mCREB-VN155 will be grown in "light" and "heavy" SILAC media, respectively. Three known CREB kinases, PKA, GSK-3β and CK-II as positive controls and housekeeping proteins such as GAPDH or actin as potential negative controls will be constructed (e.g., GAPDH fused to VC155) and then used to transfect differentially labeled LNCaP cells to form CREB-kinase complexes. The same amount of cell extracts will be subjected to GFP nanobody immunoprecipitation. Peptides will be measured by MS quantitatively. Due to specific interactions between CREB and its kinases, higher amount of CREB-kinase isolation are expected to be seen when CREB and specific kinases are used as baits than with mCREB or with negative controls. Specific kinase-CREB interactions will be distinguished by comparing relative intensity of peptides in MS spectra. Those peptides whose intensity ratios are significantly deviated from 1 will be considered and the corresponding kinases will be considered as positive hits. Statistical significance in minimum fold changes in MS measurement will be established to distinguish true kinase-substrate pairs using 3 known CREB kinases PKA, CKII and GSK-31β and 2 negative controls, GAPDH and actin. If the kinase only forms BiFC complex with the wild type of the substrate, not with the mutant form of the substrate, the software will assign a big value to indicate that essentially the complex is only measured in one isotopic form. Therefore the kinase will be identified as a strong candidate to form specific complex with the substrate.

Figure 17:
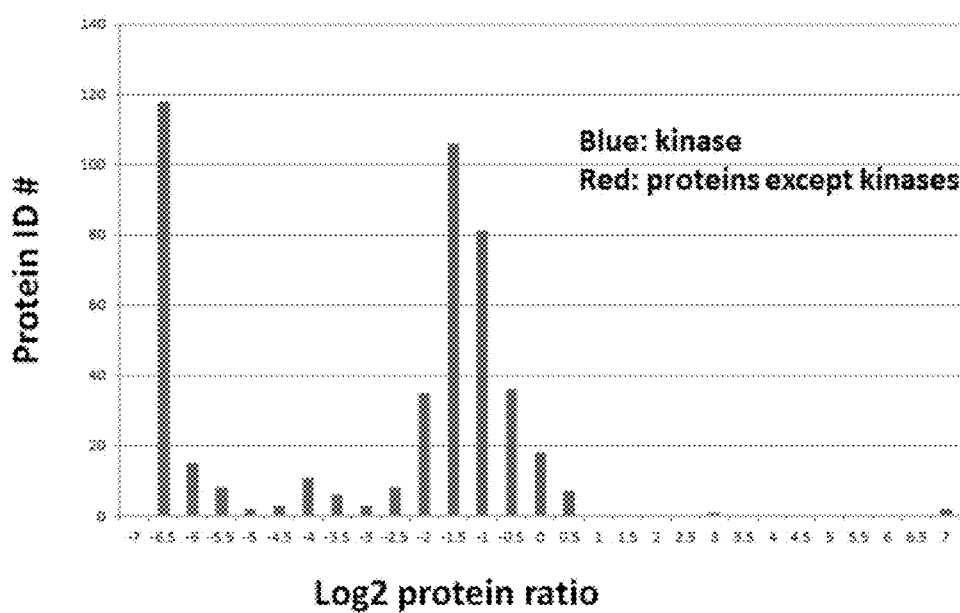
FIG. 17 is a graph plotted based on SILAC experiments (CREB Q1 sample was labeled with heavy isotopes while CREB Q2 sample was labeled with light isotopes) showing kinases were specially isolated through their interactions with CREB Q1 which contains the kinase interacting domain.
Figure 18:
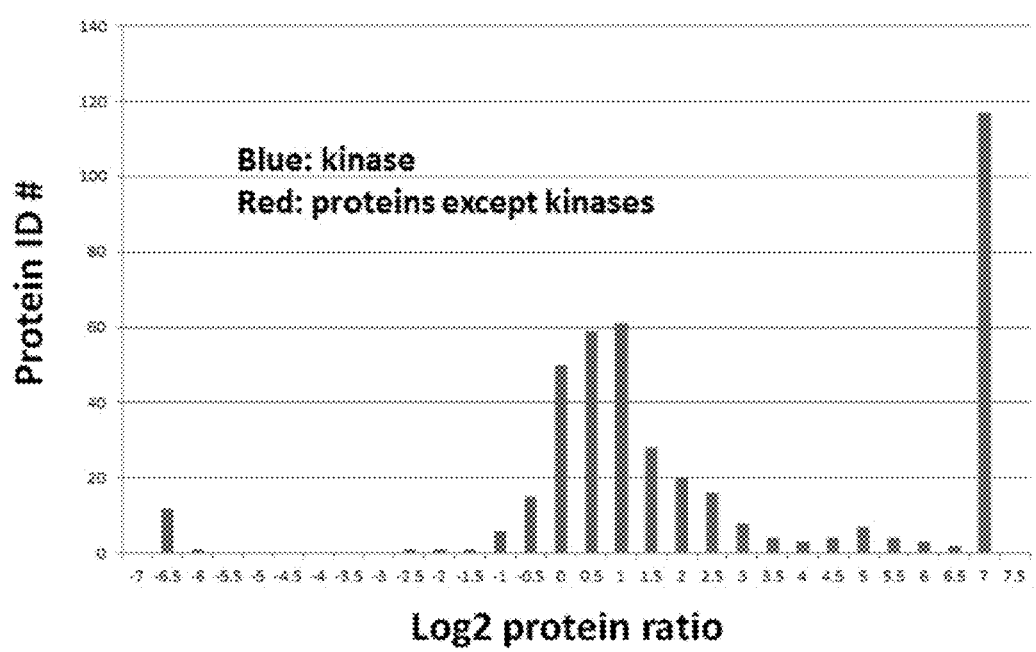
FIG. 18 is a graph plotted based on reverse SILAC experiments (CREB Q1 sample was labeled with light isotopes while CREB Q2 sample was labeled with heavy isotopes) showing kinases were specially isolated through their interactions with CREB Q1 which contains the kinase interacting domain. Reverse SILAC experiments are typically carried out to further confirm quantitative measurements.

Most kinases (about 44 kinases identified in two SILAC experiments) have a 10 fold difference (FIG. 17-18). There is a known CREB kinase ID in the overlapped proteins: PKA, LIM kinase1, CaMKI and CaMKII (FIG. 17-18).

Example 9

Specific CREB Kinases Through Phosphorylation Analysis

The multi-site phosphorylation of CREB by a diversity of protein kinases has been reported. This feature will be used to confirm specific CREB kinases. Quantitative MS experiments can add another dimension of specificity by measuring CREB phosphorylation changes on individual sites. The kinase with a positive hit can therefore be confirmed if it leads to CREB phosphorylation increase on certain sites. Compared to classical in vitro kinase assay, this approach can validate kinase-substrate relationship under the physiological condition. Because phosphorylation is a low stoichiometry event, an enrichment step may be necessary to isolate phosphopeptides before MS analysis. Therefore, as an option, after the isolation and digestion of CREB-kinase complexes, a highly efficient phosphopeptide enrichment may be applied based on PolyMAC to enrich CREB phosphopeptides followed by MS analysis (Iliuk et al., Mol Cell Proteomics 9:2162-2172, 2010). Cells were treated with Forskolin to activate PKA, and MS analysis identified 9 phosphorylation sites including 6 known sites on CREB.

To improve specificity, a new mutant in VC155 (FIG. 15) and SILAC-based quantitation to quantify interactions was introduced (FIG. 11). This is based on the assumption that mCREB-VN155 will be used to measure the background signal. There is a possibility that the background signal is still too strong to be distinguished from the specific signals from kinase-substrate interactions. As a solution, competitive binding will also be introduced into the system to distinguish between true and false-positive protein interactions. CREB-VN and mCREB-VN will be expressed in the same cells and the formation of BiFC complexes will be monitored with increasing competition from mCREB-VN whose expression level can be controlled by a Tet-ON inducible system in the same cells. The decreasing signal of CREB-VN in Western Blotting and MS analysis via the GFP nanobody immunopurification experiment with increasing competition from mCREB-VN may indicate that the interaction largely comes from VN and VC association. The strategy will be examined thoroughly using both known kinases as positive controls and housekeeping proteins as the potential negative control.

Example 10

Factors in Establishing the FCMS Sensitivity Using Known CREB Kinases

The data herein on the sensitivity of FCMS (FIG. 15) indicate FCMS has good sensitivity for the identification of known CREB kinases and for a typical library screening. This Example proposes three approaches to even further improve sensitivity of the methods of the invention. The first approach is the upgrade to a UPLC system from a nanoLC system. Ultra-high pressure/performance liquid chromatography (UPLC) achieves high coverage of proteome samples through the use of longer columns and smaller particle size that generate more theoretical plates, leading to a higher sensitivity and higher resolution. This should result in a minimum of 3-5 times increase in sensitivity. This will also facilitate the analyses of phosphorylation sites which typically have low stoichiometry. The second approach to further improve the sensitivity is to optimize the sample preparation procedure for the isolation of BiFC complexes. In MS-based analyses, the sensitivity is typically compromised by high abundant proteins whose peptides overshadow co-eluting low abundant peptides. The third and last approach to improve the FCMS sensitivity is the application of specific data acquisition methods in MS analyses. Considering proteins of interest in the sample will be CREB and its interacting kinases, the sample, if the isolation of BiFC is relatively clean, will not be complicated and therefore predicted peptides from CREB can be included and its potential kinases in the Inclusion List which forces the instrument to look for peaks even if they are overshadowed by high abundant peptides. Another data acquisition method, termed Selected Reaction Monitoring (SRM) (Surinova et al., Nat Protoc, (8):1602-19, 2013; and. Picotti et al., Nat Methods, 9(6):555-66, 2012), will also be explored to improve the detection sensitivity. SRM is a targeted MS approach that focuses on known or predicted peptides and their fragments. It typically requires a specific mass spectrometer configuration, triple quardrupole (QQQ) instrument, for this type of experiments.

Example 11

Construct Kinase LIB-cDNA-VC155

Figure 16:
FIG. 16 shows an agarose gel characterization of kinase Lib-cDNA-VC155. M: marker. 1-19: plasmid DNA were isolated from 19 colonies and digested with XhoI and EcoRI.

The data herein indicate that the FCMS method has sufficient sensitivity for library screening with the size of several hundred up to one thousand proteins (FIG. 14). A human kinase open reading frame (ORF) collection will be used to construct retrovirus-based kinase BiFC expression vectors. The collection was created by Broad Institute and distributed by Addgene (Lubonja R, et al. A public genome-scale lentiviral expression library of human ORFs. Yang X, Boehm J S, Yang X, Salehi-Ashtiani K, Hao T, Shen Y, Nature Methods. 2011). It consists of 559 distinct human kinases and kinase-related protein ORFs in pDONR-223 Gateway Entry vectors. All clones are clonal isolates and have been end-read sequenced to confirm identity. The cDNAs encoding all 559 kinases cannot be used directly by Gateway cloning. Primers will be designed to amplify each of the cDNAs by removing the stop codon. A Tet-ON inducible system will first be used to establish stable cell lines that can be induced to express FLAG-CREB-VN155 or FLAG-mCREB-VN155 by tetracycline. The cDNA sub-library encoding 559 kinases will be fused to VC155. Because fusion proteins can significantly reduce interaction-independent complementation, VC155 will be fused to the C-terminal end of kinase cDNAs. The cDNA encoding VC155 will be first sub-cloned into the pRetro-LIB, and then the cDNA encoding kinases will be PCR amplified and sub-cloned upstream of the cDNA encoding VC155. This will allow for expression of kinases as fusions with VC155. As shown in FIG. 16, the smears under the band of digested vector are different inserts in each colony, illustrating successful construction of the target library. The library will be further characterized through other biochemical methods to assure the quality of the library. In the first step, stable cell lines that can be induced to express FLAG-CREB-VN155 or FLAG-mCREB-VN155 will be cultured and induced with tetracycline first for 24 h, and then infected with retroviral kinase cDNAs. Cells after infection for 48 h will be examined by fluorescence microscopy. The quality of the library and the expression level of fused proteins in transfected cells will be examined using Western Blotting on selected kinases.

Quality control and sensitivity are the two concerns for the construction of any typical library. Since the retrovirus titer of the kinase library will be important to the screening, the experimental conditions will be optimized to generate high-titer retroviral particles (at least 106 units/ml). The viral supernatant will be concentrated to at least $5 \times 10^8$ units/ml for transient transduction. Greater than 108 cells will be infected with greater than $5 \times 10^8$ of viral particles. This will ensure that at least $2 \times 10^5$ cells will be infected with the virus encoding one kinase during the screening of the kinase library for adequate sensitivity.

Tagging proteins can sometimes preclude formation of specific interactions. BiFC addresses this issue typically through tagging target proteins at alternative terminals. To address that concern, a similar strategy will be used by expressing proteins with tags at N- or C-terminus. Several known CREB kinases will first be used to examine the effect of tags and construct the kinase library with VC-155 at their N- and the equivalent library at their C-terminus. CREB will be constructed to have VN-155 tags at its N-terminal and at its C-terminal end.

Example 12

Library Screening to Identify CREB Direct Upstream Kinases

Although assays based on protein fragment complementation have previously been attempted as potential screening methods to identify unknown protein-protein interactions, they have some severe limitations. Conceivably, cells that have positive protein-protein interactions have to be sorted cleanly and genetic materials need to be isolated and sequenced to identify the potential interacting proteins. This can be a bottleneck and time consuming step to identify unknown protein-protein interactions in BiFC approaches. Proper controls are difficult to implement in high throughput screening method and it is difficult to evaluate the false positive rate. On the other hand, methods of the invention are particularly appealing because the use of a GFP nanobody to isolate BiFC complexes provides a convenient strategy without sorting and isolations at the cellular level. After a successful infection with the constructed kinase library and the formation of BiFC complexes is verified by fluorescence microscopy, cells will be collected without sorting and isolation. Whole cell proteins will be extracted and subject to GFP nanobody isolation followed by quantitative MS analysis, as described above and in FIG. 11. Multiple CREB kinases can be identified and quantified in a single experiment. Kinases that show statistically significant difference with CREB-VN and mCREB-VN will be considered as the positive hits. False positive rate will be estimated through the use of mCREB-VN155 in parallel.

Once a list of kinases is identified as potential CREB direct upstream kinases, any new CREB kinase will be confirmed by examining phosphorylation changes on CREB, in vitro kinase assay and other biochemical approaches. Furthermore, previous studies indicate that multiple serine/threonine residues on CREB can be phosphorylated by a diversity of protein kinases. The FCMS method will allow us to identify CREB-interacting kinases under different physiological conditions and identify the sites of phosphorylation on CREB. This will provide significant information to understand the diversity of signals to which CREB can respond on the molecular level. For example, under ionizing radiation (IR) treatment of prostate cancer cells, cells become radiation-resistant and undergo NED. This process is associated with increased phosphorylation of CREB in a dose-dependent manner. CREB in prostate cancer cells is hyper-phosphorylated on a time- and dose-dependent manner (Deng et al., Am J Cancer Res 1, 834-844, 2011; and Deng et al., Cancer research 68, 9663-9670, 2008). It is likely that multiple kinases are involved in the phosphorylation, including ataxia-telangiectasia mutated (ATM). To screen for specifically IR-induced CREB kinase activity, stable cell lines infected with the retroviral kinase cDNAs library for 24 h will be used, and subject cells to IR (2Gy). Irradiated cells will be cultured for another 24 h and harvested to isolate CREB-kinase complexes for MS analysis. The success of FCMS analysis will be able to identify ATM and other active CREB kinases and identify potential phosphorylation sites on CREB.

Once the candidate kinases are identified and phosphorylation sites are mapped, the role of the CREB kinases and the phosphorylation conferring radioresistance and NED will be determined. Mutagenesis will be performed to mutate phosphorylation sites on CREB to non-phosphorylatable mutants, or to mimic phosphorylation of CREB. These mutants will be transiently expressed in LNCaP cells before subjecting to fractionated IR for one week. Radiation-induced cell death will be quantified by MTT assays and flow cytometry analysis. For IR-induced NED, stable cell lines expressing inducible mutant CREB will be established, and their effect on IR-induced NED will be similarly evaluated. Second, BiFC experiments will be used to verify whether CREB-kinase interaction can be induced by fractionated IR. For this purpose, cells will be transfected with plasmids encoding CREB-VN155 and kinase-VC155 and subjected to fractionated IR. Fluorescent images will be acquired and BiFC signal will be quantified. Third, to study the role of CREB phosphorylation by the identified protein kinases, monoclonal antibodies that specifically recognize phospho-CREB at particular sites will be used. These antibodies will be used to determine the phosphorylation status of CREB at the endogenous level during the course of IR-induced NED by immunoblotting analysis. Fourth, a pharmacological approach will be used to evaluate the role of identified kinases in IR-induced NED. Specifically, LNCaP cells will be subjected to fractionated IR in the presence or absence of a specific kinase inhibitor and the effect on IR-induced NED will be similarly evaluated.

A potential issue is that false positive protein-protein interactions could be generated during in-vitro sample treatment (e.g. lysis and in vitro incubation), in particular for a high throughput experiment where sensitivity is critical. The use of GFP nanobody is advantageous to address this issue through extremely short time for in vitro treatment (<5 min versus multiple hours for a typical IP). In addition, the problem can be addressed by choosing a lysis condition that does not lead to VN155-VC155 self-assembly. For example a higher concentration of detergent in lysis buffer or the addition of free VN155 (VC155) in the lysis buffer, along with short incubation time, can be used to minimize BiFC complex formation in vitro.

What is claimed is:
1. A method for analyzing two transiently interacting proteins in a sample, wherein a first protein is fused with a first fragment of a reporter protein and a second protein is fused with a second fragment of said reporter protein, the method comprising:

conducting a protein-fragment complementation assay on the sample to form a protein-protein complex transiently under physiological conditions;

separating the complex from the sample using a moiety that specifically binds a fused form of the reporter protein but not either of the first and second proteins individually, and applying a washing condition to the sample that removes the first and second proteins in their free form while preserving the complex; and quantitatively analyzing at least one protein of the complex using a mass spectrometry technique.

2. The method according to claim 1, wherein the reporter protein is a bimolecular fluorescence protein.

3. The method according to claim 1, wherein separating comprises:

exposing the complexes to one or more solid supports, each solid support comprising the moiety that specifically binds the fused form of the reporter protein; and washing away remaining components of the sample.

4. The method according to claim 3, wherein the moiety is an antibody that specifically binds the fused form of the reporter protein.

5. The method according to claim 4, wherein the antibody is selected from the group consisting of an anti-fluorescence protein antibody, a nanobody and a variable single domain antibody fragment ($V_H H$).

6. The method according to claim 3, wherein the fused form of the reporter protein comprises a first member of a binding pair, and the moiety is a second member of the binding pair.

7. The method according to claim 3, wherein the solid supports are beads.

8. The method according to claim 3, wherein prior to the analyzing step, the method further comprises:

eluting the complexes from the solid supports; and digesting the proteins to from peptides.

9. The method according to claim 1, wherein one protein of the complex is a kinase.

10. A method for analyzing two transiently interacting proteins in a sample, wherein a first protein is fused with a first fragment of a reporter protein and a second protein is fused with a second fragment of said reporter protein, the method comprising:

conducting a protein-fragment complementation assay on the sample to form a protein-protein complex transiently under physiological conditions, and the assay is conducted in the presence of a competitor;

separating the complex from the sample using a moiety that specifically binds a fused form of the reporter protein but not either of the first and second proteins individually, and applying a washing condition to the sample that removes the first and second proteins in their free form while preserving the complex; and quantitatively analyzing a protein of the complex using a mass spectrometry technique.

11. The method according to claim 10, wherein the reporter protein is a bimolecular fluorescence protein.

12. The method according to claim 10, wherein separating comprises:

exposing the complexes to one or more solid supports, each solid support comprising the moiety that specifically binds the fused form of the reporter protein; and washing away remaining components of the sample.

13. The method according to claim 12, wherein the moiety is an antibody that specifically binds the fused form of the reporter protein.

14. The method according to claim 13, wherein the antibody is selected from the group consisting of an anti-fluorescence protein antibody, a nanobody and a variable single domain antibody fragment (VHH).

15. The method according to claim 12, wherein the fused form of the reporter protein comprises a first member of a binding pair, and the moiety is a second member of the binding pair.

16. The method according to claim 12, wherein the solid supports are beads.

17. The method according to claim 12, wherein prior to the analyzing step, the method further comprises:

eluting the complexes from the solid supports; and digesting the proteins to from peptides.

18. The method according to claim 10, wherein one protein of the complex is a kinase.

19. The method according to claim 1, wherein the analyzing step provides an amino acid modification status of at least one protein in the complex.

* * * * *